United States Patent
Sugawara

(10) Patent No.: US 10,010,365 B2
(45) Date of Patent: Jul. 3, 2018

(54) SURGICAL TREATMENT INSTRUMENT

(71) Applicant: OLYMPUS CORPORATION, Hachioji-shi, Tokyo (JP)

(72) Inventor: Tateyuki Sugawara, Yokohama (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/274,540

(22) Filed: Sep. 23, 2016

(65) Prior Publication Data

US 2017/0007314 A1 Jan. 12, 2017

Related U.S. Application Data

(63) Continuation of application No. PCT/JP2015/073699, filed on Aug. 24, 2015.

(30) Foreign Application Priority Data

Oct. 9, 2014 (JP) ................. 2014-208198

(51) Int. Cl.
*A61B 18/14* (2006.01)
*A61B 18/12* (2006.01)
(Continued)

(52) U.S. Cl.
CPC ...... *A61B 18/14* (2013.01); *A61B 17/320068* (2013.01); *A61B 18/1206* (2013.01);
(Continued)

(58) Field of Classification Search
CPC ............ A61B 18/1402; A61B 18/1206; A61B 2018/00994; A61B 2018/1467
See application file for complete search history.

(56) References Cited

U.S. PATENT DOCUMENTS

2004/0010249 A1* 1/2004 Truckai .................. A61B 18/14
606/41
2008/0312715 A1* 12/2008 Asirvatham ....... A61B 18/1492
607/45
(Continued)

FOREIGN PATENT DOCUMENTS

JP 2002-306507 A 10/2002
JP 2005-501597 A 1/2005
(Continued)

OTHER PUBLICATIONS

JB Calvert, Electrical Discharges, Last revised Sep. 29, 2005. Accessed Jul. 14, 2017. http://www.physics.csbsju.edu/tk/370/jcalvert/dischg.htm.html*
(Continued)

*Primary Examiner* — Ronald Hupczey, Jr.
*Assistant Examiner* — Bo Ouyang
(74) *Attorney, Agent, or Firm* — Oliff PLC

(57) ABSTRACT

A handpiece is a surgical treatment instrument to treat a living tissue using electric energy and includes a probe configured to extend in a longitudinal direction from a proximal end portion to a distal end portion, and enabled to apply the electric energy to the living tissue and a shaft rod member configured to be disposed inside the probe, a portion of the shaft rod member closest to the probe being located away from the probe by a distance at which a discharge occurs at a voltage lower than a voltage at which a spark discharge occurs between the probe and the shaft rod member and higher than a voltage at which an arc discharge occurs between the probe and the shaft rod member.

15 Claims, 11 Drawing Sheets

(51) Int. Cl.
  *A61B 17/32* (2006.01)
  *A61B 18/00* (2006.01)
(52) U.S. Cl.
  CPC ............... *A61B 18/1402* (2013.01); *A61B 2018/00601* (2013.01); *A61B 2018/00994* (2013.01); *A61B 2018/1467* (2013.01)

(56) References Cited

U.S. PATENT DOCUMENTS

| | | | |
|---|---|---|---|
| 2013/0325002 A1 | 12/2013 | Strauss et al. | |
| 2015/0327921 A1* | 11/2015 | Govari | A61B 5/0538 600/373 |

FOREIGN PATENT DOCUMENTS

| | | |
|---|---|---|
| JP | 2005-205002 A | 8/2005 |
| JP | 2014-514000 A | 6/2014 |
| WO | 03/020145 A1 | 3/2003 |
| WO | 2012/116891 A1 | 9/2012 |

OTHER PUBLICATIONS

Nov. 17, 2015 Search Report issued in International Patent Application No. PCT/JP2015/073699.
Jun. 21, 2016 Decision to Grant Patent issued in Japanese Patent Application No. 2016-510896.

\* cited by examiner

SURGICAL TREATMENT INSTRUMENT

CROSS REFERENCE TO RELATED APPLICATION

This application is a continuation application of PCT/JP2015/073699 filed on Aug. 24, 2015 and claims benefit of Japanese Application No. 2014-208198 filed in Japan on Oct. 9, 2014, the entire contents of which are incorporated herein by this reference.

BACKGROUND OF THE INVENTION

1. Field of the Invention

The present invention relates to a surgical treatment instrument, and more particularly, to a surgical treatment instrument that outputs a high-frequency current.

2. Description of the Related Art

Conventionally, treatment apparatuses such as an electric knife using high-frequency current are used in surgical operations when performing dissection or hemostasis of a living tissue. Furthermore, as disclosed in Japanese Patent Application Laid-Open Publication No. 2002-306507, a treatment apparatus provided with an ultrasound supply section that supplies ultrasound vibration to an electrode in addition to a high-frequency current has also been proposed in recent years. The electric knife is an apparatus configured to radiate a high-frequency current onto a living tissue from a distal end of an electrode at a tip of the electric knife to perform dissection or hemostasis of the living tissue using an arc discharge or Joule heat generated by the high-frequency current. Electric knives are used in various fields such as general surgery and endoscopic surgery.

SUMMARY OF THE INVENTION

A surgical treatment instrument according to an aspect of the present invention is a surgical treatment instrument for treating a living tissue using electric energy, including a first electrode configured to extend in a longitudinal direction from a proximal end portion to a distal end portion, and enabled to apply the electric energy to the living tissue, and a second electrode configured to be disposed inside or outside the first electrode, a portion of the second electrode closest to the first electrode being located away from the first electrode by a distance at which a discharge occurs at a voltage lower than a voltage at which a spark discharge occurs between the first and second electrodes and higher than a voltage at which an arc discharge occurs between the first and second electrodes.

DETAILED DESCRIPTION OF THE PREFERRED EMBODIMENT(S)

Hereinafter, embodiments of the present invention will be described with reference to the accompanying drawings.

First Embodiment

Figure 1:
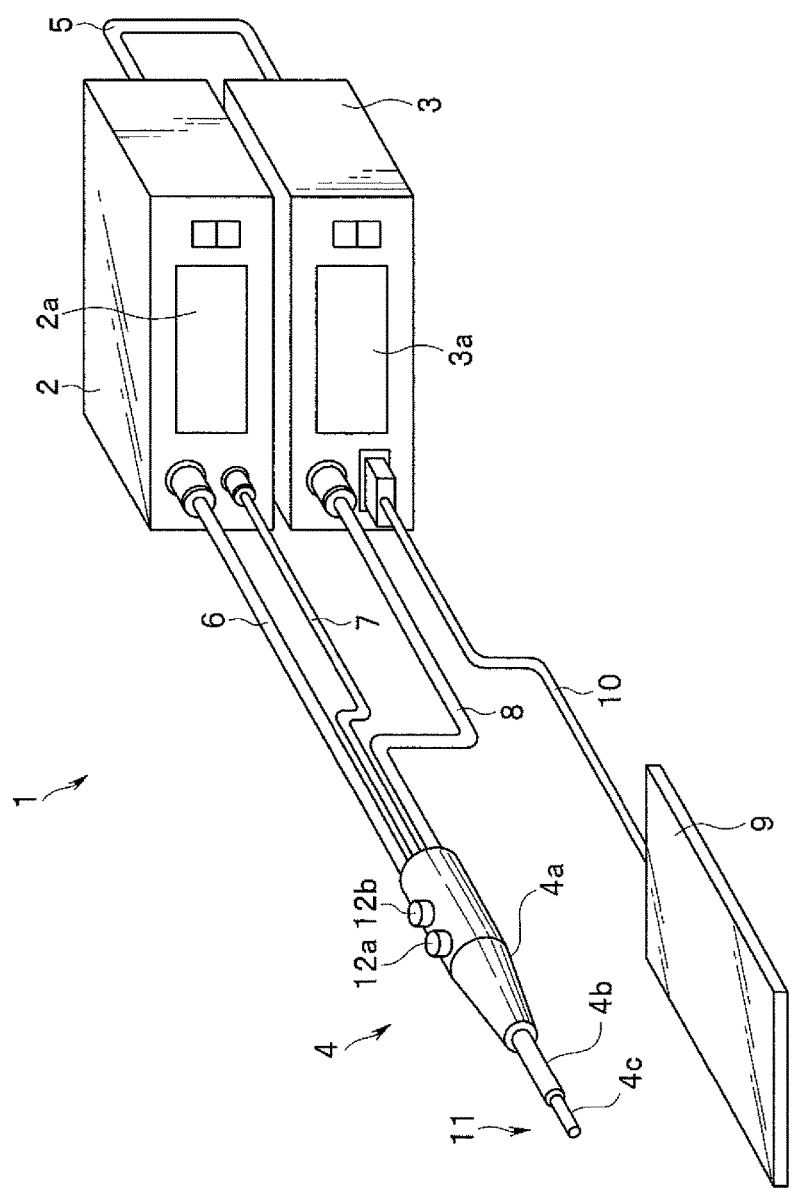
FIG. 1 is a configuration diagram illustrating a configuration of a surgical treatment system 1 according to a first embodiment of the present invention.

FIG. 1 is a configuration diagram illustrating a configuration of a surgical treatment system 1 according to the present embodiment. The surgical treatment system 1 is mainly constructed of an ultrasound drive apparatus 2, a high-frequency drive apparatus 3, and a handpiece 4. The handpiece 4 is a surgical treatment instrument for treating a living tissue using electric energy. The high-frequency drive apparatus 3 is a power supply configured to supply electric energy to the handpiece 4.

The ultrasound drive apparatus 2 and the high-frequency drive apparatus 3 are connected together via a communication cable 5. The handpiece 4 which is a surgical treatment instrument is connected to the ultrasound drive apparatus 2 via a connector using an output connection cable 6 and a SW connection cable 7 and further connected to the high-frequency drive apparatus 3 via a connector using an output connection cable 8.

Furthermore, a counter electrode plate 9 is connected to the high-frequency drive apparatus 3 via a connector using a connection cable 10. The ultrasound drive apparatus 2 is provided with an operation display panel 2a and the high-frequency drive apparatus 3 is provided with an operation display panel 3a.

The handpiece 4 is a monopolar surgical treatment instrument including an exterior member 4a made of an insulating material, an insulating tube 4b configured to extend from a distal end of the exterior member 4a and a probe 4c configured to extend from a distal end of the insulating tube 4b, and configured to output a high-frequency current from the probe 4c as electric energy.

The handpiece 4 includes an ultrasound transducer configured to generate ultrasound vibration inside the exterior member 4a and the probe 4c is enabled to output ultrasound vibration as well. Thus, the distal end portion of the probe 4c constitutes a treatment section 11 enabled to output ultrasound vibration and output a high-frequency current.

The exterior member 4a is provided with operation switches 12a and 12b. The operation switches 12a and 12b are operation sections to instruct output in different output modes. In the ultrasound drive apparatus 2 and the high-frequency drive apparatus 3, the operation switches 12a and 12b select one of high-frequency current output, ultrasound vibration output and simultaneous output of high-frequency current and ultrasound vibration, and set respective output levels. An operator operates the operation switches 12a and 12b, and can thereby perform treatment using the treatment section 11 with the selected output and output level.

Figure 2:
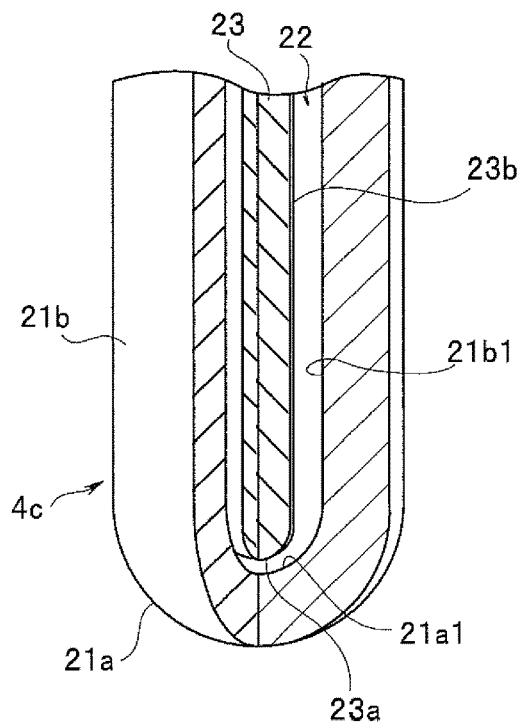
FIG. 2 is a cross-sectional view along an axial direction of a distal end portion of a probe 4c according to the first embodiment of the present invention.

FIG. 2 is a cross-sectional view of a distal end portion of the probe 4c in an axial direction. The probe 4c is made of a conductive metallic material such as titanium. The probe 4c is an electrode configured to extend in a longitudinal direction from a proximal end portion to a distal end portion, and enabled to apply electric energy to a living tissue. The probe 4c is a hollow, elongated shaft member with a closed distal end. A distal end portion 21a of the probe 4c has a spherical crown shape and a shaft portion 21b has a cylindrical shape. That is, the probe 4c has a cylindrical shape with the closed distal end portion 21a.

A hollow portion 22 in the probe 4c is formed of an inside surface 21a1 of the distal end portion 21a of the probe 4c and an inner surface 21b1 of the shaft portion 21b on the distal end side, and a space sealed with a seal member which is not shown on the proximal end side. The distal end side of the hollow portion 22 has a sagittal shape and a portion from the distal end side toward the proximal end side of the hollow portion 22 has a cylindrical shape. The interior of the hollow portion 22 is filled with air. Note that the interior of the hollow portion 22 may also be filled with an inert gas other than air.

A shaft rod member 23 is inserted into the hollow portion 22 without touching the inside surface 21a1 of the distal end portion 21a of the probe 4c or the inner surface 21b1 of the shaft portion 21b, disposed inside the cylindrical probe 4c and fixed at the proximal end portion. That is, when the shaft rod member 23 is inserted in the probe 4c and fixed, the probe 4c and the shaft rod member 23 are insulated from each other with air in the hollow portion 22.

The shaft rod member 23 is made of a conductive metallic material such as titanium. The distal end portion 23a of the shaft rod member 23 has a spherical crown shape and the shaft portion 23b has a cylindrical shape.

Figure 3:
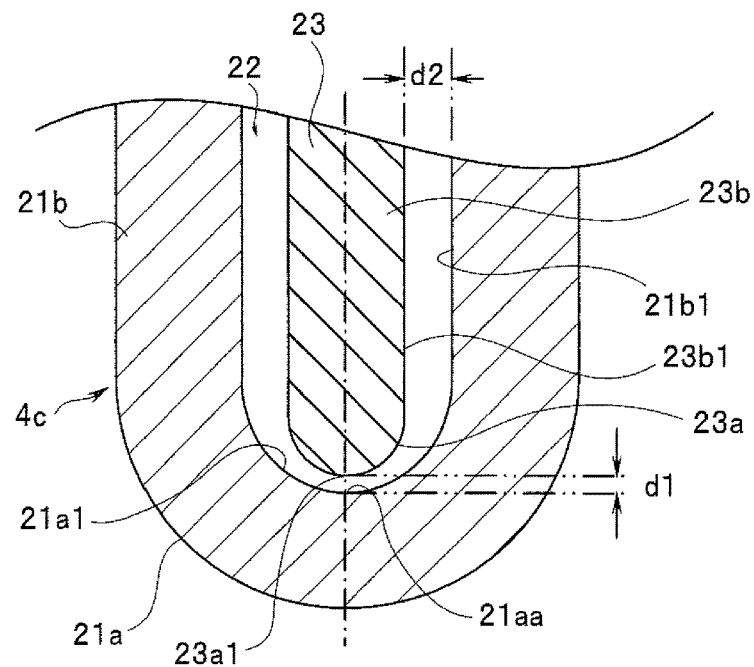
FIG. 3 is a cross-sectional view of the distal end portion of the probe 4c according to the first embodiment of the present invention.

FIG. 3 is a cross-sectional view of the distal end portion of the probe 4c. A distance between the distal end portion 23a of the shaft rod member 23 and the inside surface 21a1 of the closed distal end portion 21a of the probe 4c is d1. More specifically, a distance between a vertex 23a1 of the distal end portion 23a of the shaft rod member 23 and a base point 21as of the inside surface 21a1 of the distal end portion 21a of the probe 4c is d1.

A distance between an outer circumferential face 23b1 of the shaft portion 23b of the shaft rod member 23 and the inner surface 21b1 of the shaft portion 21b of the probe 4c is d2. Here, d2>d1.

The distance d1 is set as follows.

An arc discharge occurs between the surface of the probe 4c and a living tissue, and the distance d1 is set to such a distance that no spark discharge may occur between the surface of the probe 4c and the living tissue.

More specifically, according to Paschen's law, a voltage V at which a discharge occurs is a function of a distance d between electrodes and a pressure p of a gas. In the case of FIG. 3, the hollow portion 22 is an air layer, and when it is assumed that a voltage of the probe 4c when an arc discharge occurs between the surface of the probe 4c and the living tissue is Varc, and a voltage of the probe 4c when a spark discharge occurs is Vspa, if a set voltage Vset of the probe 4c is set to be greater than Varc and smaller than Vspa, the distance d1 becomes a function of the set voltage Vset and the pressure p of air.

A voltage Vglo when a glow discharge occurs is higher than the voltage Varc when an arc discharge occurs, a voltage Vcor when a corona discharge occurs is higher than the voltage Vglo and lower than the voltage Vspa. Therefore, the set voltage Vset is preferably higher than the voltage Varc and lower than the voltage Vglo.

Therefore, by setting the distance d1 to a distance at which a discharge occurs between the base point 21aa of the inside surface 21a1 of the probe 4c and the vertex 23a1 of the distal end portion 23a of the shaft rod member 23 before producing such a voltage that causes a spark discharge between the outside surface of the probe 4c and the living tissue to let the charge to escape toward the shaft rod member 23, it is possible to avoid any spark discharge from occurring between the probe 4c and the living tissue and prevent any voltage exceeding a predetermined value from applying to the living tissue. That is, setting the distance between portions closest to each other between the probe 4c and the shaft rod member 23 to the aforementioned distance d1 prevents any voltage exceeding the set voltage Vset from applying to the probe 4c.

Thus, the shaft rod member 23 constitutes an electrode which is disposed inside the probe 4c, a vertex 23a1 of the electrode which is a portion closest to the probe 4c is located away from the probe 4c by the distance d1 at which a discharge occurs at Vset which is a voltage lower than Vspa which is a voltage at which a spark discharge occurs between the electrode and the probe 4c and higher than Varc which is a voltage at which an arc discharge occurs between the electrode and the probe 4c.

Note that the distance d2 is greater than the distance d1 to avoid such a situation that when the shaft rod member 23 is inserted into the hollow portion 22 and fixed, since the shaft portion 21b of the probe 4c is long, a positioning error may occur between the proximal end portion and the distal end portion of the probe 4c, causing the distance d2 to become smaller than the distance d1.

More specifically, when the shaft rod member 23 is inserted into the probe 4c and the proximal end portion of the shaft rod member 23 is fixed to the probe 4c, the distance d1 can be set to a predetermined design value with position accuracy of the shaft rod member 23 with respect to the probe 4c in the axial direction of the probe 4c. However, since the shaft portion 23b of the shaft rod member 23 is long, when the shaft rod member 23 is inserted into the hollow portion 22 and fixed, a difference may be produced in the position of the probe 4c with respect to the inner surface 21b1 between the proximal end portion and the distal end portion of the shaft rod member 23. That is, the distance to the inner surface 21b1 of the probe 4c of the shaft rod member 23 may differ between the proximal end side and the distal end of the probe 4c in a direction orthogonal to the axis of the probe 4c.

Thus, the distance d2 is set to a magnitude that absorbs such a positional difference so that the accuracy of the gap to prevent any spark discharge at the distal end of the probe 4c may be secured by the distance d1.

Therefore, the distance d2 may be equal to the distance d1 when the positional accuracy of the shaft rod member 23 can be secured.

As described above, since at least part of the conductive shaft rod member 23 is provided in the hollow portion 22 inside the probe 4c so as to keep the distance d1, even if a voltage exceeding a set voltage applies to the probe 4c, the charge is discharged to the shaft rod member 23 in the probe 4c, preventing the occurrence of a discharge exceeding the set voltage between the living tissue and the probe 4c.

Thus, according to the aforementioned present embodiment, it is possible to implement a handpiece which is a surgical treatment instrument that prevents a voltage applied to the electrode from exceeding a predetermined value.

Next, modifications of the present embodiment will be described.

Modification 1

Modification 1 relates to a surgical treatment instrument in which the probe is insulated from the shaft rod member using an insulating member and a discharge is caused to occur between the distal end face of the shaft rod member and the inside surface of the distal end portion of the probe 4c. Note that in the present modification, the same components as those of the aforementioned first embodiment are assigned the same reference numerals and description is omitted and different components will be described.

Figure 4:
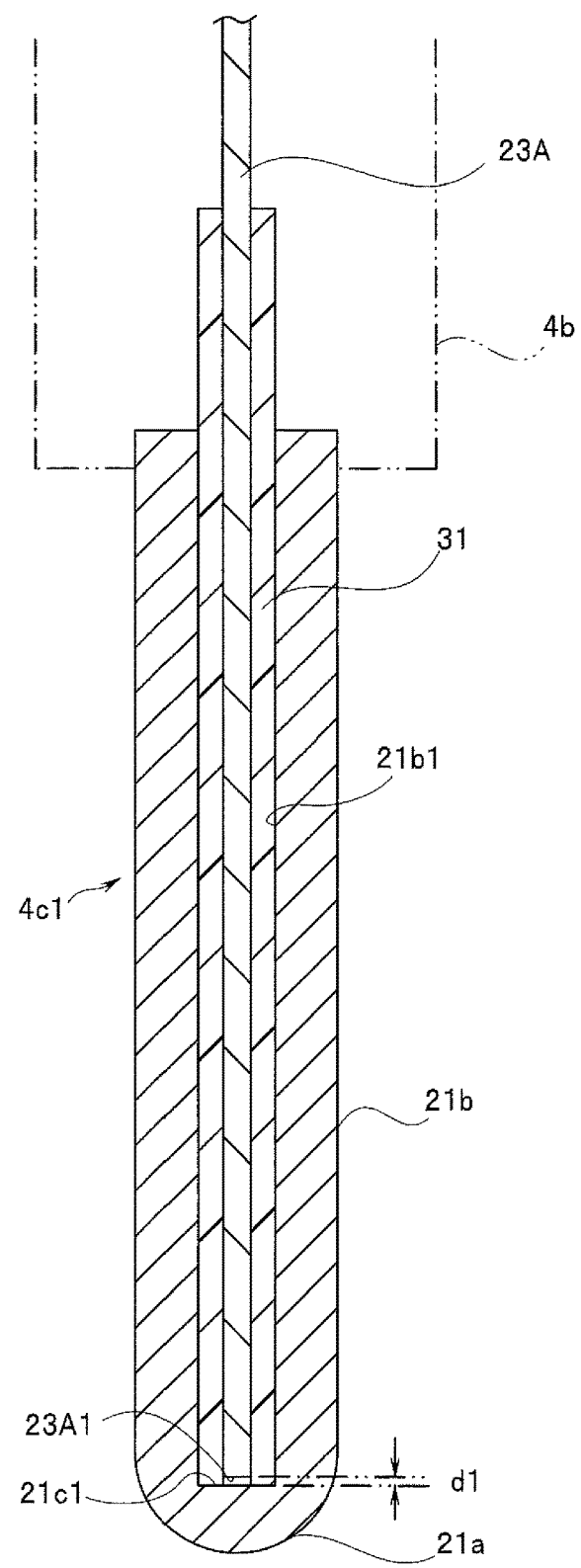
FIG. 4 is a cross-sectional view of a probe 4c1 according to modification 1 of the first embodiment of the present invention.

FIG. 4 is a cross-sectional view of a probe 4c1 according to modification 1 of the first embodiment.

The probe 4c1 is made of a conductive metal material such as titanium. The probe 4c1 is an electrode configured to extend in a longitudinal direction from a proximal end portion to a distal end portion, and enabled to apply electric energy to a living tissue. The probe 4c1 is a hollow, elongated shaft member with a closed distal end. An outside shape of the probe 4c1 is the same as the aforementioned probe 4c.

A flat inside surface 21c1 is formed on a distal end side of the hollow portion in the probe 4c.

A shaft rod member 23A is inserted into the hollow portion inside the probe 4c and an insulating member 31 is disposed between the shaft rod member 23A and the inner surface 21b1 of the probe 4c. The shaft rod member 23A is made of a conductive metallic material such as titanium.

That is, the insulating member 31 has a cylindrical shape, the shaft rod member 23A is inserted inside the insulating member 31 and the shaft rod member 23A is covered with the cylindrical insulating member 31. The insulating member 31 is made of resin such as PTFE.

A distal end face 23A1 of the shaft rod member 23A has a flat surface. The shaft rod member 23A is disposed and fixed inside the probe 4c1 so that the distal end face 23A1 of the shaft rod member 23A is located away from the inside surface 21c1 of the probe 4c1 by the aforementioned distance d1. A space surrounded by the distal end face 23A1 of the shaft rod member 23A, the insulating member 31 and the inside surface 21c1 of the probe 4c1 is a sealed space.

In present modification 1, the hollow portion 22 of the first embodiment is substituted by the cylindrical insulating member 31, the distance between the distal end face 23A1 of the shaft rod member 23A and the inside surface 21c1 of the probe 4c1 is set to d1 to prevent any spark discharge from occurring at the distal end of the probe 4c.

That is, the inside surface 21c1 of the closed distal end portion 21a of the probe 4c1 has a flat surface portion, the distal end face 23A1 of the shaft rod member 23A has a flat surface portion and the distance d1 is a distance between the two flat surface portions disposed opposite to each other.

Present modification 1 also has effects similar to those of the aforementioned first embodiment and uses the cylindrical insulating member 31, and can thereby improve positional accuracy of the shaft rod member 23A in the probe 4c1 and has an effect of facilitating manufacturing.

Modification 2

Modification 2 relates to a surgical treatment instrument for which the area of the distal end portion of the shaft rod member is increased. In present modification 2, the area of the distal end portion of the shaft rod member 23 of the first embodiment is greater than the area of the distal end portion of the first embodiment.

Figure 5:
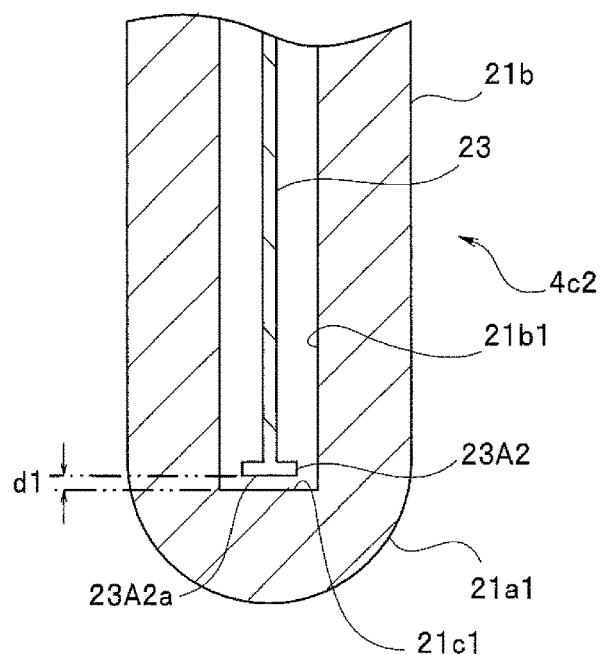
FIG. 5 is a cross-sectional view of a probe 4c2 according to modification 2 of the first embodiment of the present invention.

FIG. 5 is a cross-sectional view of a probe 4c2 according to modification 2 of the first embodiment. Note that in the present modification, the same components as those in the aforementioned first embodiment and modification 1 are assigned the same reference numerals, description is omitted and different components will be described.

The probe 4c2 is made of a conductive metallic material such as titanium. The probe 4c2 is an electrode configured to extend in a longitudinal direction from a proximal end portion to a distal end portion, and enabled to apply electric energy to a living tissue. The probe 4c2 is a hollow, elongated shaft member with a closed distal end. An outside shape of the probe 4c2 is the same as the aforementioned probe 4c.

An outward flange portion 23A2 of an enlarged diameter is formed at the distal end portion of the shaft rod member 23 inserted into the hollow portion inside the probe 4c2. The distal end side of the outward flange portion 23A2 constitutes a flat surface portion. The hollow portion in the probe 4c2 is a sealed space.

The shaft rod member 23 is disposed and fixed inside the probe 4c2 so that the distal end face of the outward flange portion 23A2 at the distal end portion of the shaft rod member 23A is located away from the inside surface 21c1 of the probe 4c2 by the distance d1.

That is, the inside surface 21c1 of the closed distal end portion 21a of the probe 4c2 has a flat surface portion, a distal end face 23A2a portion of the shaft rod member 23 has the outward flange portion 23A2 which is an enlarged diameter part having a flat surface portion and the distance d1 is a distance between the two flat surface portions disposed opposite to each other.

Thus, present modification 2 also has effects similar to those of the aforementioned first embodiment, and since the area of the distal end face of the shaft rod member 23 is large, modification 2 also has an effect of stabilizing discharge.

Second Embodiment

In the surgical treatment instrument of the first embodiment, the hollow portion of the probe is formed from the distal end portion to the proximal end portion, whereas in the present embodiment, the hollow portion is formed only at a portion on the distal end side.

Since a surgical treatment system of the present embodiment has a configuration similar to that of the surgical treatment system 1 of the first embodiment, the same components as those of the aforementioned first embodiment are assigned the same reference numerals, description is omitted and different components will be described.

Figure 6:
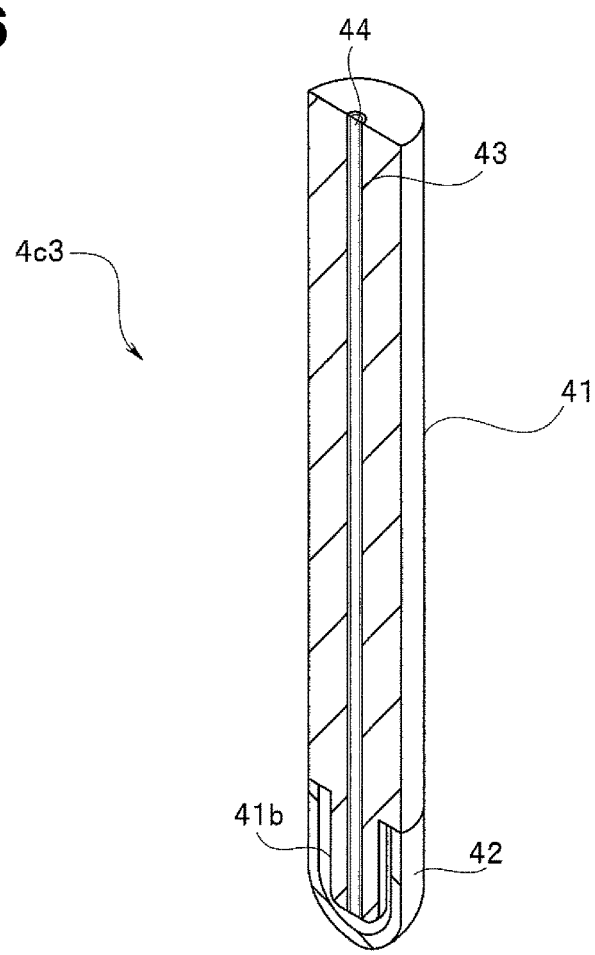
FIG. 6 is a perspective cross-sectional view of a probe 4c3 according to a second embodiment of the present invention.
Figure 7:
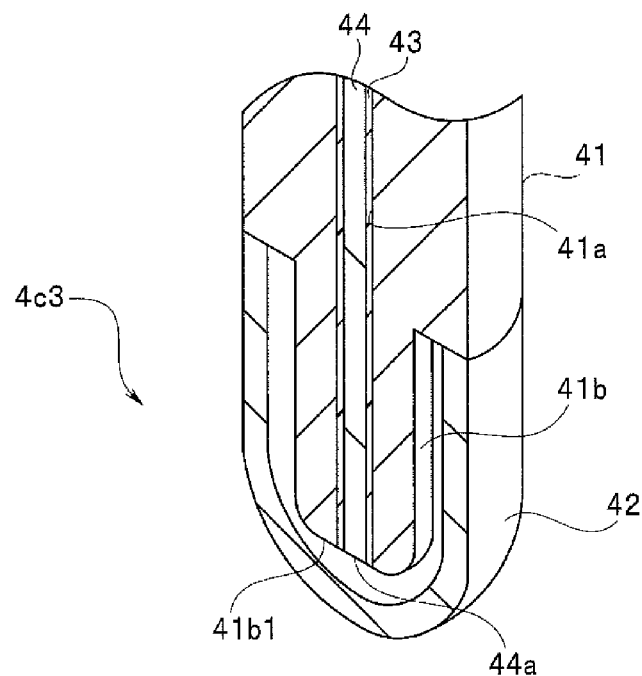
FIG. 7 is a perspective cross-sectional view of a distal end portion of the probe 4c3 according to the second embodiment of the present invention.
Figure 8:
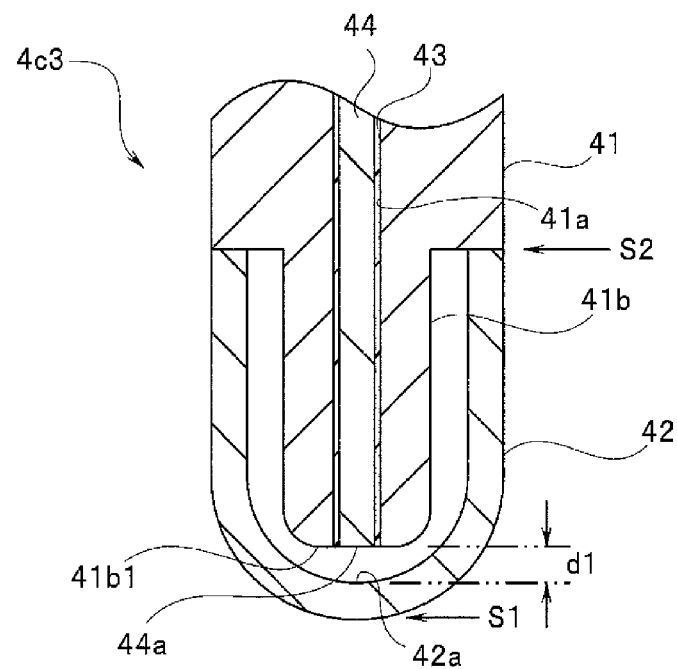
FIG. 8 is a cross-sectional view of the distal end portion of the probe 4c3 according to the second embodiment of the present invention.

FIG. 6 is a perspective cross-sectional view of a probe 4c3 according to the present embodiment. FIG. 7 is a perspective cross-sectional view of a distal end portion of the probe 4c3 according to the present embodiment. FIG. 8 is a cross-sectional view of the distal end portion of the probe 4c3 according to the present embodiment.

The probe 4c3 is constructed of a rod member 41 in which a hole 41a (FIG. 7 and FIG. 8) is formed in a central part along an axial direction and a cap member 42 which is placed to cover the distal end portion of the rod member 41 and fixed. The rod member 41 and the cap member 42 are made of a conductive metallic material such as titanium. The probe 4c3 is an electrode configured to extend in a longitudinal direction from a proximal end portion to a distal end portion, and enabled to apply electric energy to a living tissue.

A shaft rod member 44 covered with an insulating member 43 is inserted into the hole 41a of the rod member 41 and fixed. The insulating member 43 is made of resin such as PTFE. The shaft rod member 44 is made of a conductive metallic material such as titanium.

A protruding portion 41b is formed at a distal end portion of the rod member 41 and a distal end face 44a of the shaft rod member 44 is exposed to an opening of a distal end face 41b1 of the protruding portion 41b.

The cap member 42 is a cylindrical member whose distal end side has a closed spherical crown shape. When the cap member 42 is fixed to the rod member 41, the distal end face 44a of the shaft rod member 44 does not touch an inside surface of the cap member 42. A space between the inner surface of the cap member 42 and an outer circumferential face of the protruding portion 41b of the rod member 41 is a sealed space filled with a gas such as air or inert gas.

The cap member 42 is fixed to the rod member 41 through bonding using an adhesive or metal joining or the like. Alternatively, the cap member 42 may be fixed to the rod member 41 through screwing between a threaded part formed on the inner surface of the cap member 42 and a threaded part formed on the outer circumferential face of the protruding portion 41b of the rod member 41.

The shaft rod member 44 is disposed and fixed inside the rod member 41 of the probe 4c3 so that the distal end face 44a of the shaft rod member 44 is located away from an inside base portion 42a of the cap member 42 by a distance d1 when the cap member 42 is fixed to the rod member 41. That is, the shaft rod member 44 is disposed inside the probe 4c3 so as not to touch the probe 46 and the distance d1 is a distance between the distal end portion of the shaft rod member 44 and the inside base portion 42a which is an inside surface on the distal end side of the cap member 42.

Thus, the shaft rod member 44 constitutes an electrode whose distal end face 44a which is a portion closest to the probe 4c3 is located away from the probe 4c3 by the distance d1 at which a discharge occurs at Vset which is a voltage lower than Vspa which is a voltage at which a spark discharge occurs between the electrode and the probe 4c3 and higher than Varc which is a voltage at which an arc discharge occurs between the electrode and the probe 4c3.

Furthermore, since the probe 4c3 also outputs ultrasound vibration, the length of the cap member 42 in the axial direction is set so that a position S1 of the distal end portion of the cap member 42 becomes a swelled part of ultrasound vibration and a position S2 of a joint between the cap member 42 and the rod member 41 becomes a node part of ultrasound vibration.

Thus, according to the aforementioned present embodiment, it is possible to implement a handpiece which is a surgical treatment instrument that prevents a voltage applied to the electrode from exceeding a predetermined value.

Since the cap member 42 is provided at the distal end of the probe 4c3 and the distance between the cap member 42 and the shaft rod member 44 is set to d1, the present embodiment also has an effect of easily achieving the accuracy of the distance d1.

Next, a modification of the present embodiment will be described.

MODIFICATION

A modification relates to a surgical treatment instrument for which shapes of the shaft rod member and the cap member of the aforementioned embodiment are changed.

Figure 9:
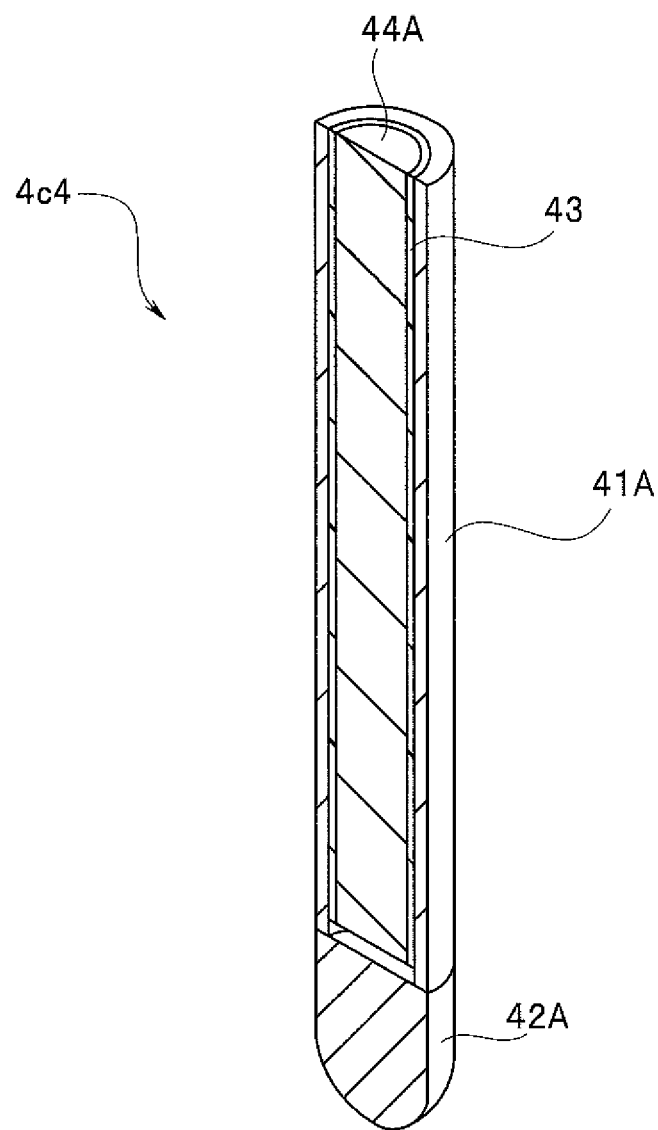
FIG. 9 is a perspective cross-sectional view of a probe 4c4 according to a modification of the second embodiment of the present invention.
Figure 10:
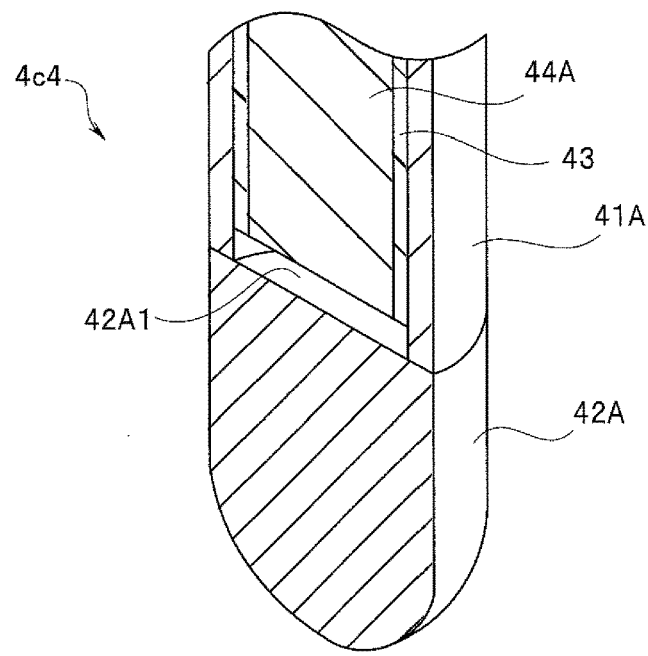
FIG. 10 is a perspective cross-sectional view of a distal end portion of the probe 4c4 according to the modification of the second embodiment of the present invention.
Figure 11:
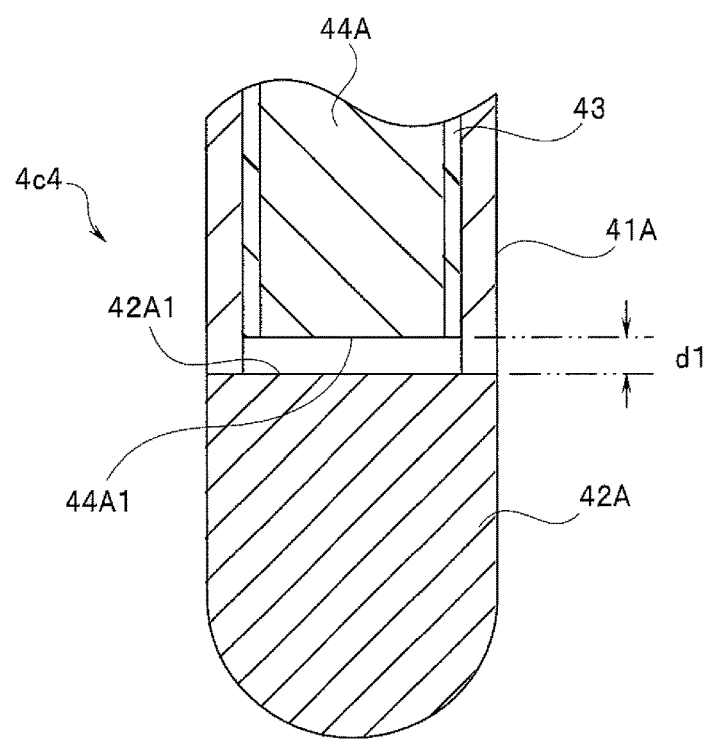
FIG. 11 is a cross-sectional view of the distal end portion of the probe 4c4 according to the modification of the second embodiment of the present invention.

FIG. 9 is a perspective cross-sectional view of a probe 4c4 according to the modification of the second embodiment. FIG. 10 is a perspective cross-sectional view of the distal end portion of the probe 4c4 according to the present modification. FIG. 11 is a cross-sectional view of the distal end portion of the probe 4c4 according to the present modification.

The probe 4c4 is made of a conductive metallic material such as titanium. The probe 4c4 is an electrode configured to extend in a longitudinal direction from a proximal end portion to a distal end portion, and enabled to apply electric energy to a living tissue.

The probe 4c4 includes a rod member 41A and a distal end fixing member 42A which is fixed to the distal end side of the rod member 41A. The rod member 41A of the probe 4c4 has a cylindrical shape. The distal end fixing member 42A is a cylindrical member whose distal end portion has a spherical crown shape and whose proximal end portion has a flat surface portion 42A1.

A shaft rod member 44A is a cylindrical member having a greater diameter than the shaft rod member 44 of the second embodiment. A distal end face 44A1 of the shaft rod member 44A has a flat surface. An outer circumferential portion of the shaft rod member 44A is covered with an insulating member 43. The shaft rod member 44A is made of a conductive metallic material such as titanium.

As described above, the distal end fixing member 42A is bonded, metal-joined or screwed. A space surrounded by the distal end face 44A1 of the shaft rod member 44A, the insulating member 43 and an inside surface of the rod member 41A is a sealed space.

When the distal end fixing member 42A is fixed to the rod member 41A1, the flat surface portion 42A1 of the distal end fixing member 42A and the distal end face 44A1 of the shaft rod member 44A are placed opposite to face each other so that both surfaces are arranged in parallel.

The shaft rod member 44A is disposed within the probe 4c4 and fixed so that the flat surface portion 42A1 of the distal end fixing member 42A is located away from the distal end face 44A1 of the shaft rod member 44A by the aforementioned distance d1.

That is, the probe 4c4 includes the rod member 41A and the distal end fixing member 42A provided at the distal end of the rod member 41A and including the proximal end face having the flat surface portion 42A1. The shaft rod member 44A is disposed inside the cylindrical probe 4c4 so as not to touch the probe 4c4 and includes the distal end face 44A1 having a flat surface portion on the distal end side. The distance d1 is a distance between the proximal end face having the flat surface portion 42A1 of the distal end fixing member 42A and the distal end face 44A1 having the flat surface portion of the shaft rod member 44A.

Thus, in addition to the effects of the aforementioned second embodiment, the present modification has an effect of stabilizing discharge more easily.

Third Embodiment

In the surgical treatment instrument according to the second embodiment, the hollow portion is formed on the distal end side, whereas in the present embodiment, the hollow portion is formed only on the proximal end side.

Since the surgical treatment system of the present embodiment has a configuration similar to that of the surgical treatment system according to the second embodiment, the same components as those in the aforementioned second embodiment are assigned the same reference numerals, description is omitted and different components will be described.

Figure 12:
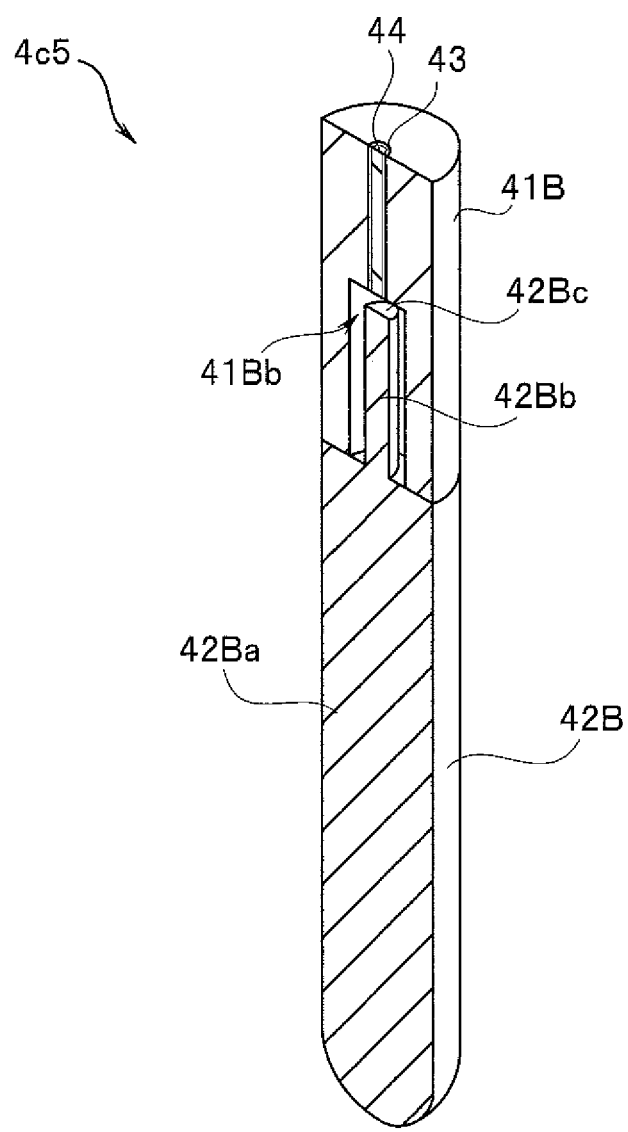
FIG. 12 is a perspective cross-sectional view of a probe 4c5 according to a third embodiment of the present invention.
Figure 13:
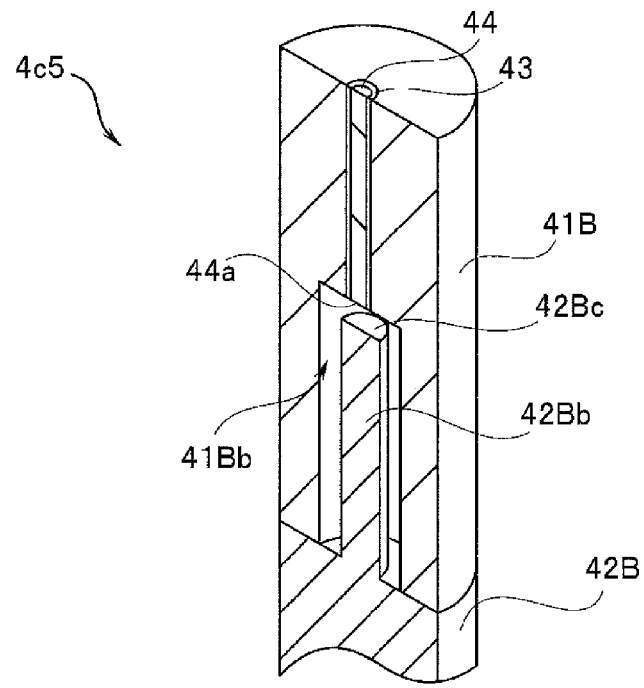
FIG. 13 is a perspective cross-sectional view of a distal end portion of the probe 4c5 according to the third embodiment of the present invention.
Figure 14:
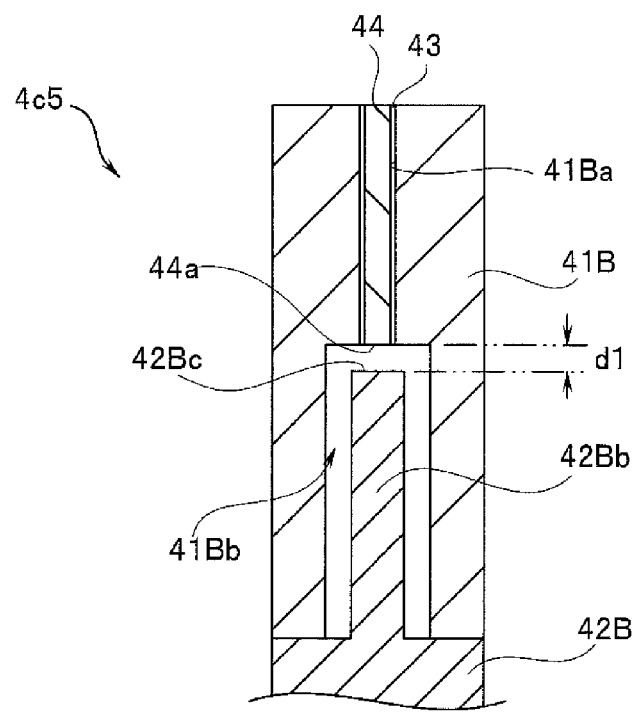
FIG. 14 is a cross-sectional view of the distal end portion of the probe 4c5 according to the third embodiment of the present invention.

FIG. 12 is a perspective cross-sectional view of a probe 4c5 according to the present embodiment. FIG. 13 is a perspective cross-sectional view of a distal end portion of the probe 4c5 according to the present embodiment. FIG. 14 is a cross-sectional view of the distal end portion of the probe 4c5 according to the present embodiment.

The probe 4c5 is constructed of a rod member 41B in which a hole 41Ba is formed at a central part along an axial direction and a distal end fixing member 42B fixed to a distal end portion of the rod member 41B. The rod member 41B and the distal end fixing member 42B are made of a conductive metallic material such as titanium. The probe 4c5 is an electrode configured to extend in a longitudinal direction from a proximal end portion to a distal end portion, and enabled to apply electric energy to a living tissue.

A shaft rod member 44 covered with an insulating member 43 is inserted into the hole 41Ba of the rod member 41B and fixed.

A concave portion 41Bb is formed at a distal end portion of the rod member 41B and a distal end face 44a of the shaft rod member 44 is exposed to a bottom surface portion of the concave portion 41Bb.

The distal end fixing member 42B is a cylindrical member having a spherical crown shape whose distal end side is closed. The distal end fixing member 42B has a rod-shaped portion 42Ba which is longer than the aforementioned distal end fixing member 42A. Furthermore, a protruding portion 42Bb configured to protrude in the axial direction is formed at the proximal end portion of the distal end fixing member 42B. When the distal end fixing member 42B is fixed to the rod member 41B, the protruding portion 42Bb does not touch the inside surface of the concave portion 41Bb. A space between the outer circumferential face of the protruding portion 42Bb of the distal end fixing member 42B and the inner surface of the concave portion 41Bb of the rod member 41B is filled with a gas such as air or inert gas.

The interior of the concave portion 41Bb in which the protruding portion 42Bb is disposed is a sealed space. That is, the probe 4c5 includes the rod member 41B having the concave portion 41Bb on the distal end side and the distal end fixing member 42B placed to cover the distal end of the rod member 41B. The shaft rod member 44 is disposed inside the concave portion 41Bb so as not to touch the probe 4c5. The aforementioned distance d1 is a distance between the distal end portion of the shaft rod member 44 and the distal end fixing member 42B.

The distal end fixing member 42B is fixed to the rod member 41B through an adhesive, metal joining or the like. Alternatively, the distal end fixing member 42B may also be fixed to the rod member 41B through screwing between a threaded part formed on an outer circumferential face of the protruding portion 42Bb of the distal end fixing member 42B and a threaded part formed on the inner circumferential face of the concave portion 41Bb of the rod member 41B.

The shaft rod member 44 is disposed and fixed within the rod member 41B of the probe 4c5 so that when the distal end fixing member 42B is fixed to the rod member 41B, the distal end face 44a of the shaft rod member 44 is located away from a proximal end face 42Bc of the protruding portion 42Bb of the distal end fixing member 42B by the aforementioned distance d1.

That is, the shaft rod member 44 constitutes an electrode configured to be disposed inside the probe 4c5, whose distal end face 44a which is a portion closest to the probe 4c5 is located away from the probe 4c5 by the distance d1 at which a discharge occurs at Vset which is a voltage lower than Vspa which is a voltage at which a spark discharge occurs between the shaft rod member 44 and the probe 4c5 and higher than Varc which is a voltage at which an arc discharge occurs between the shaft rod member 44 and the probe 4c5.

Thus, according to the aforementioned present embodiment, it is possible to implement a handpiece which is a surgical treatment instrument that prevents a voltage applied to the electrode from exceeding a predetermined value.

In the case of the present embodiment, since the shaft rod member 44 is shorter than the shaft rod member 44 of the second embodiment, the accuracy of the distance d1 can be improved and assembly of the long probe 4c5 is easier.

Fourth Embodiment

The surgical treatment instruments according to the first to third embodiments have a gap of the aforementioned distance d1 for discharge inside the probe, whereas a surgical treatment instrument according to the present embodiment has a gap of the aforementioned distance d1 for discharge with respect to an outer circumferential face of a simple rod-shaped probe.

The surgical treatment system according to the fourth embodiment has a configuration similar to that of the surgical treatment system 1 of the first embodiment. The only difference lies in the configuration of the probe at the distal end of the surgical treatment instrument.

Figure 15:
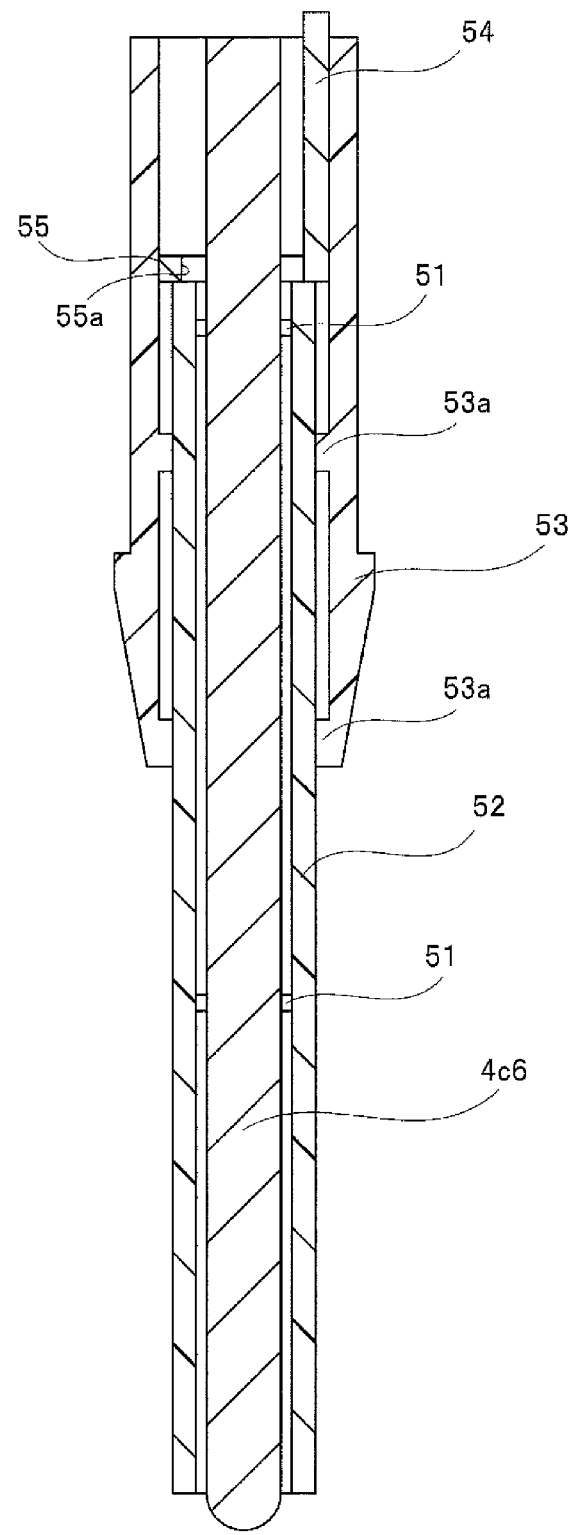
FIG. 15 is a cross-sectional view of a distal end portion of a surgical treatment instrument according to a fourth embodiment of the present invention.
Figure 16:
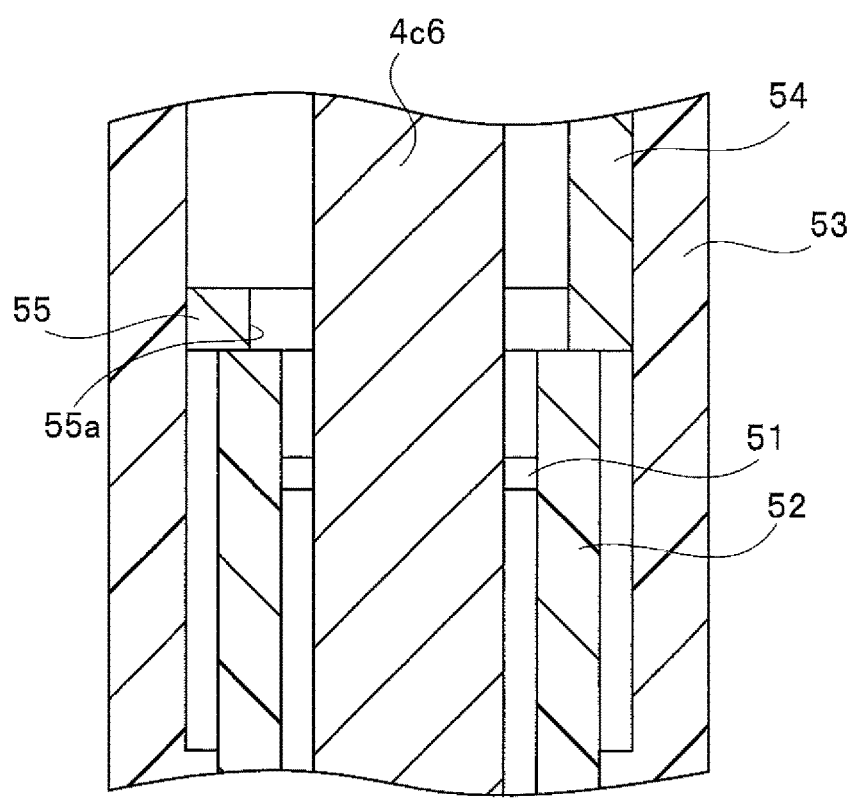
FIG. 16 is a cross-sectional view of a gap portion of a proximal end portion according to the fourth embodiment of the present invention.

FIG. 15 is a cross-sectional view of a distal end portion of the surgical treatment instrument according to the present embodiment. FIG. 16 is a cross-sectional view of a gap portion of the proximal end portion according to the present embodiment.

The probe 4c6 is a cylindrical member whose distal end has a spherical crown shape. A plurality of (two in FIG. 15) rubber O-shaped rings 51 are attached to an outer circumferential portion of the probe 4c6. A cylindrical insulating member 52 is placed to cover the probe 4c6 via the O-shaped rings 51. The probe 4c6 is made of a conductive metallic material such as titanium. The probe 4c6 is an electrode configured to extend in a longitudinal direction from a proximal end portion to a distal end portion, and enabled to apply electric energy to a living tissue. The insulating member 52 is made of resin such as PTFE.

The probe 4c6 is inserted into the insulating member 52 and fixed to such an extent that the distal end portion of the probe 4c6 slightly protrudes from an opening of the distal end portion of the cylindrical insulating member 52.

A cylindrical resin outer sheath 53 is provided so as to cover the proximal end portion of the insulating member 52. An inward flange portion 53a is formed at the distal end portion and at some midpoint of the outer sheath 53. The cylindrical insulating member 52 is fixed to the outer sheath 53 with the inner circumferential face of the inward flange portion 53a coming into close contact with the outer circumferential face of the insulating member 52 and fixed.

A conductive shaft rod member 54 is inserted on the proximal end side of the outer sheath 53. A conductive ring-shaped portion 55 is attached to the distal end portion of the shaft rod member 54. While in contact with the proximal end face of the insulating member 52, the ring-shaped portion 55 remains in close contact with the inner circumferential face of the outer sheath 53. The probe 4c6 extends from the insulating member 52 toward the proximal end side inside the outer sheath 53.

In the ring-shaped portion 55, the thickness of the ring-shaped portion 55 is set so that the distance between a circumferential face portion 55a on the side opposite to the inner circumferential face on the side on which the shaft rod member 54 is attached and the surface of the probe 4c6 becomes the aforementioned d1.

The probe 4c6 is fixed to the cylindrical insulating member 52 via the O-shaped ring 51 and the insulating member 52 is fixed to the outer sheath 53 via the inward flange portion 53a. The ring-shaped portion 55 is fixed to the inner circumferential face of the outer sheath 53.

A portion of the inner circumferential face portion 55a of the ring-shaped portion 55 closest to the probe 4c6 is positioned so as to be located away from the surface of the probe 4c6 by the distance d1.

As described above, the probe 4c6 is a rod member and the shaft rod member 54 is disposed outside the probe 4c6 so as not to touch the probe 4c6. The distance d1 is a distance between the outer circumferential face of the probe 4c6 and the surface of the shaft rod member 54 opposite to the outer circumferential face.

Thus, the shaft rod member 54 constitutes an electrode configured to be disposed outside the probe 4c6, whose inner circumferential face portion 55a which is a portion closest to the probe 4c6 is located away from the probe 4c6 by the distance d1 at which a discharge occurs at Vset which is a voltage lower than Vspa which is a voltage at which a spark discharge occurs between the shaft rod member 54 and the probe 4c6 and higher than Varc which is a voltage at which an arc discharge occurs between the shaft rod member 54 and the probe 4c6.

As described above, according to the present embodiment, it is possible to implement a handpiece which is a surgical treatment instrument that prevents a voltage applied to the electrode from exceeding a predetermined value.

Moreover, the aforementioned probe 4c6 of the present embodiment has the same structure as that of the conventional probe, and thereby has an effect of eliminating the need for processing on the probe itself as shown in the first to third embodiments.

As described above, according to the aforementioned embodiments and modifications, it is possible to implement a handpiece which is a surgical treatment instrument and a surgical treatment system that prevent a voltage applied to the electrode from exceeding a predetermined value.

The present invention is not limited to the aforementioned embodiments, but various modifications and alterations or the like can be made without departing from the spirit and scope of the present invention.

What is claimed is:

1. A surgical treatment instrument for treating a living tissue using electric energy, comprising:
   a first electrode configured to extend in a longitudinal direction from a proximal end portion to a distal end portion, and enabled to apply the electric energy for an arc discharge to the living tissue; and
   a second electrode configured to be disposed inside or outside the first electrode, a portion of the second electrode closest to the first electrode configured to be located away from the first electrode by a distance at which a discharge occurs between the first and second electrodes before a voltage would be produced by the first electrode causing a spark discharge between the first electrode and living tissue, thereby preventing the spark discharge to the living tissue, the distance also being a distance at which discharge does not occur between the first and second electrodes when the first electrode produces an arc discharge to the living tissue.

2. The surgical treatment instrument according to claim 1, wherein the first electrode has a cylindrical shape including a closed distal end portion, and
   the second electrode is disposed inside the first electrode having the cylindrical shape so as not to touch the first electrode.

3. The surgical treatment instrument according to claim 2, wherein the distance is a distance between a distal end portion of the second electrode and an inside surface of the closed distal end portion of the first electrode.

4. The surgical treatment instrument according to claim 3, wherein the inside surface of the closed distal end portion of the first electrode comprises a first flat surface portion,
   the distal end portion of the second electrode comprises a second flat surface portion, and
   the distance is a distance between the first flat surface portion and the second flat surface portion disposed opposite to each other.

5. The surgical treatment instrument according to claim 4, wherein the second electrode is covered with a cylindrical insulating member.

6. The surgical treatment instrument according to claim 3, wherein the inside surface of the closed distal end portion of the first electrode comprises a first flat surface portion,
   the distal end portion of the second electrode comprises an enlarged diameter portion including a second flat surface portion, and
   the distance is a distance between the first flat surface portion and the second flat surface portion disposed opposite to each other.

7. The surgical treatment instrument according to claim 1, wherein the first electrode comprises a rod member and a cap member placed to cover a distal end of the rod member,
   the second electrode is disposed inside the first electrode so as not to touch the first electrode, and
   the distance is a distance between a distal end portion of the second electrode and an inside surface on a distal end side of the cap member.

8. The surgical treatment instrument according to claim 7, wherein the cap member is bonded, joined or screwed to the rod member.

9. The surgical treatment instrument according to claim 1, wherein the first electrode comprises a rod member and a distal end fixing member fixed to a distal end of the rod member and configured to include a first flat surface portion,
the second electrode is disposed inside the cylindrical first electrode so as not to touch the first electrode and configured to include a second flat surface portion on a distal end side, and
the distance is a distance between the first flat surface portion of the distal end fixing member and the second flat surface portion of the second electrode.

10. The surgical treatment instrument according to claim 1, wherein the first electrode comprises a rod member including a concave portion on a distal end side and a distal end fixing member fixed to a distal end of the rod member,
the second electrode is disposed inside the concave portion so as not to touch the first electrode, and
the distance is a distance between the distal end portion of the second electrode and the distal end fixing member.

11. The surgical treatment instrument according to claim 10, wherein the distal end fixing member is bonded, joined or screwed to the rod member.

12. The surgical treatment instrument according to claim 1, wherein the first electrode is a rod member,
the second electrode is disposed outside the first electrode so as not to touch the first electrode, and
the distance is a distance between an outer circumferential face of the first electrode and a surface of the second electrode opposite to the outer circumferential face.

13. The surgical treatment instrument according to claim 1, wherein the surgical treatment instrument comprises a counter electrode plate, the surgical treatment instrument is configured to output a high-frequency current from the first electrode as the electric energy, and the counter electrode plate is configured to receive the high-frequency current, and
the counter electrode plate is provided at a position separate from the first electrode and the second electrode.

14. The surgical treatment instrument according to claim 13, wherein the first electrode outputs ultrasound vibration.

15. The surgical treatment instrument according to claim 1, wherein the distance is smaller than a distance between an inner circumferential side face of the first electrode and an outer circumferential side face of the second electrode.

* * * * *